United States Patent [19]
Chow

[11] Patent Number: 5,480,408
[45] Date of Patent: Jan. 2, 1996

[54] ENDOSCOPIC SURGICAL KIT FOR RELEASE OF TRIGGER FINGER

[76] Inventor: James C. Y. Chow, 3001 Caroline St., Mount Vernon, Ill. 62864

[21] Appl. No.: 135,462

[22] Filed: Oct. 12, 1993

[51] Int. Cl.$^6$ .............................. A61B 17/32; A61B 1/00
[52] U.S. Cl. .............................. 606/167; 604/160; 606/170
[58] Field of Search ............................ 606/79, 148, 167, 606/170, 185, 222, 223; 604/160, 164, 264, 272; 128/4

[56] References Cited

U.S. PATENT DOCUMENTS

| | | | |
|---|---|---|---|
| 1,321,011 | 11/1919 | Cottes | 606/223 |
| 2,365,647 | 12/1944 | Ogburn | 606/167 |
| 4,963,147 | 10/1990 | Agee et al. | 606/170 |
| 4,966,143 | 10/1990 | Meinershagen | 606/223 |
| 5,029,573 | 7/1991 | Chow | 606/170 |
| 5,089,000 | 2/1992 | Agee et al. | 606/170 |
| 5,269,796 | 12/1993 | Miller et al. | 606/167 |
| 5,273,024 | 12/1993 | Menon et al. | 128/4 |
| 5,292,330 | 3/1994 | Shutt | 606/167 |
| 5,318,582 | 6/1994 | Chow | 606/170 |
| 5,323,765 | 6/1994 | Brown | 606/170 |

FOREIGN PATENT DOCUMENTS

| | | | |
|---|---|---|---|
| 1324657 | 7/1987 | U.S.S.R. | 606/167 |
| 2203341 | 10/1988 | United Kingdom | 606/167 |

*Primary Examiner*—David M. Shay
*Assistant Examiner*—Nancy Mulcare
*Attorney, Agent, or Firm*—Polster, Lieder, Woodruff & Lucchesi

[57] ABSTRACT

A surgical kit for performing trigger finger release surgery. A flexor tendon (T) passes through the palm (P) of a person's hand (H) to a finger (F) or thumb (B). Constriction of a protective sheath (E) around the tendon causes the trigger finger condition. For a person suffering from trigger finger, a path (1) of the impaired tendon is first identified. A puncture site is then located for insertion of one end of a hollow, curved cannula (1) into the palm. The cannula is pushed through the palm with a first puncture hole (U) being made where the instrument enters into the palm, and a second puncture hole (U') where the cannula exits from the palm. The cannula is routed through the palm such that the path (8) of the cannula passes through the sheath. The cannula is left in place and an arthroscope (9) and a surgical knife (11) are inserted into respective ends of the instrument. The surgeon views the surgical site through a monitor (10) to which the arthroscope is attached. The knife has a cutting blade brought to bear by the surgeon on the sheath. The cannula has a longitudinally extending slot (2) through which the surgeon both views the site and moves the knife against the sheath. After the surgery is complete, the arthroscope and knife are removed from the cannula and the cannula is withdrawn from the palm. The size of the cannula is such that after its withdrawal, the puncture wounds made do not require stitches to close them. As the wounds heal, no scars are formed.

9 Claims, 5 Drawing Sheets

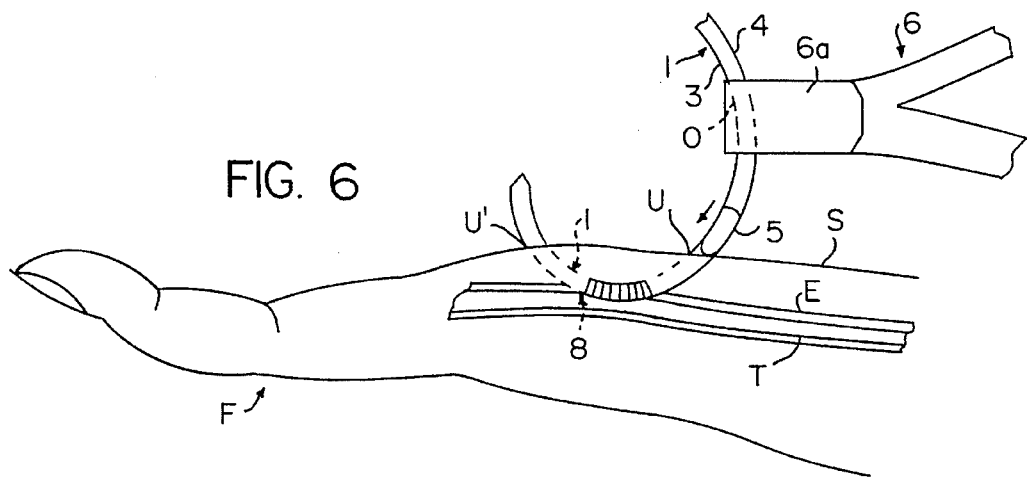
FIG. 6
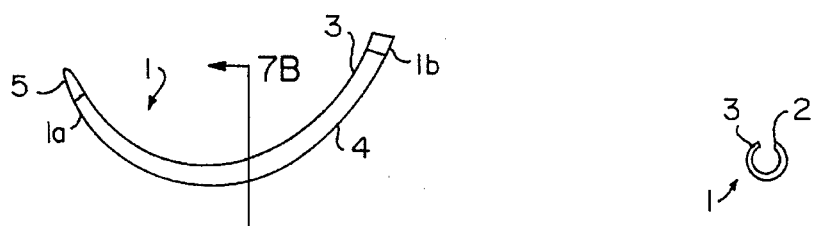
FIG. 7A
FIG. 7B
FIG. 7C
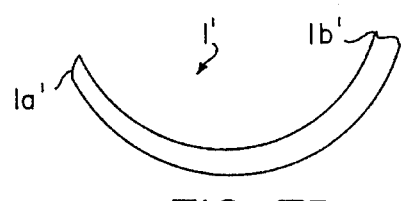
FIG. 7D
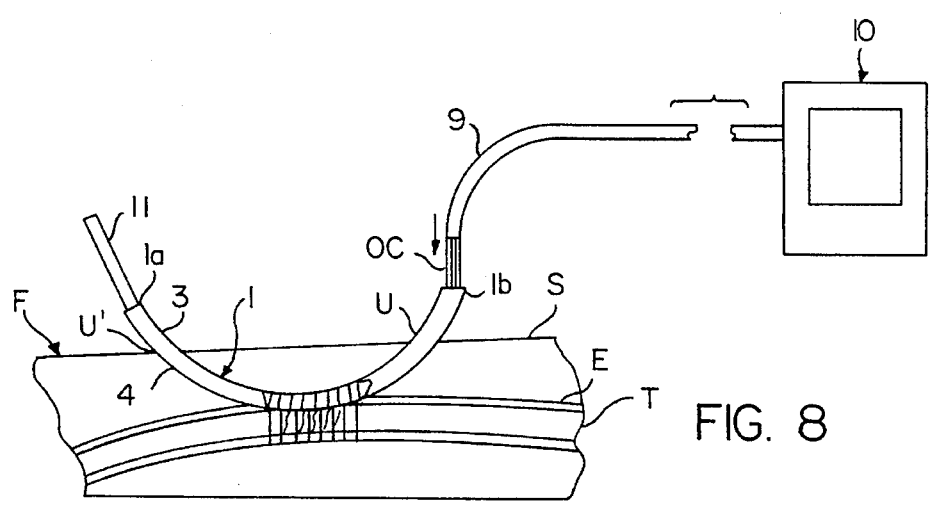
FIG. 8

5,480,408

ENDOSCOPIC SURGICAL KIT FOR RELEASE OF TRIGGER FINGER

BACKGROUND OF THE INVENTION

This invention relates to arthroscopic surgery techniques and, more particularly, to a surgical kit used to perform trigger finger release and trigger thumb release surgery.

Trigger finger or trigger thumb is a condition which typically effects the middle aged. It manifests itself as an involuntary movement of a finger or thumb in response to a sensed pressure in the palm of the hand. Although the condition may be congenital, it is seldom found in children over the age of two. If combined with a collagen disease which attacks the connective tissue in the hand, several fingers of a person's hand may be involved. The condition most often effects the middle finger or ring finger; although, as the name implies, the thumb is also often involved. If a nodule is formed, or a fusiform (spindle-like) swelling occurs, a restriction, or narrowing, or stenosis of the flexor tendon results. This narrowing occurs adjacent the sheath or theca covering the tendon at the distal crease in the palm of the hand. The nodule usually appears at the point where the tendon enters the proximal annulus at the level of the metacarpophalangeal joint. Applying pressure to the nodule, such as by palpatating it, causes the nodule to move with the tendon. If the thumb is involved, the interphalangeal joint will be the one that appears to snap or lock, even though the constriction is, as noted, associated with the metacarpophangeal joint.

Sectioning of the annulus through a surgical procedure may relieve the triggering. In some instances, a partially lacerated flexor tendon will heal with a nodule large enough that there may be a recurrence of the triggering. Or, if the patient is rheumatoid, there may be complications. However, the problem is one which lends itself to a surgical solution. One problem with current surgical techniques is that they require a lengthy incision to be made in the palm of the hand to facilitate insertion of a surgical knife or scissors used to cut the sheath surrounding the flexor tendon and relieve the constriction. Once the knife or scissors is removed, stitches are required to close the wound. This results in scarring. An arthroscopic surgical method for releasing trigger finger is described in my co-pending U.S. Pat. No. 5,353,812.

SUMMARY OF THE INVENTION

Among the several objects of the present invention may be noted the provision of a surgical kit for use in an operation to relieve a trigger finger or trigger thumb condition in a patient; the provision of such surgical kit for use in an arthroscopic surgical procedure; the provision of such surgical kit to enable a surgeon to readily puncture the skin in a patient's palm at first and second spaced sites for an instrument to be inserted into the hand; the provision of such surgical apparatus to allow the surgeon to clearly and easily view the surgical site using an arthroscope; the provision of such surgical kit to allow the surgeon to readily locate a cutting instrument at the surgical site for use in releasing a distal palm pulley causing the trigger finger; the provision of such a surgical kit which allows the surgeon to make surgical incisions which are so small that after completion of the surgery no sutures are required to close the puncture holes made in the palm whereby, after healing, no scars are formed in the palm of the hand; the provision of such surgical kit which enables the surgeon to perform an endoscopic procedure as readily as previous surgical procedures used to effect similar repairs; and, the provision of such a surgical kit by which an arthroscopic surgical procedure to release trigger finger can be performed at any convenient location such as the surgeon's office, a clinic, or a hospital and requires only an attending physician and a surgical nurse or aide.

In accordance with the invention, generally stated, a surgical kit is disclosed for performing a method of trigger finger release surgery. A flexor tendon for each finger and thumb of a hand is routed through the palm of the hand. Constriction of a protective sheath around a flexor tendon causes the trigger finger condition. The routing path of the flexor tendon to the particular finger is first identified. Next, a puncture site is located along the path. A hollow, curved cannula having a longitudinally extending slot has one end inserted into the palm at the puncture site. The leading end of the cannula is then pushed back through the skin to create a second puncture hole at the exit site. The cannula is routed through the hand such that its path passes through the sheath. The cannula is left in place. One end of an arthroscope is inserted into one end of the cannula. This allows the surgeon to view the surgical site through the slot in the cannula. An athroscopic surgical knife is now inserted into the other end of the cannula. A cutting blade of the knife is movable through the slot by the surgeon to lacerate the sheath and release the trigger finger. The sheath is cut with the knife. The arthroscope and knife are now withdrawn from the cannula, and the cannula is then removed. The size of the cannula is such that after its withdrawal, the first and second puncture wounds do not require stitches to close them. And, as the wounds heal, no scars are formed. Other objects and features will be in part apparent and in part pointed out hereinafter.

BRIEF DESCRIPTION OF THE DRAWINGS

FIG. 6 is a simplified cross-sectional view of the hand illustrating one step in practicing the method;

FIG. 7A is an elevational view of a slotted cannula used in the surgery, FIG. 7B is a sectional view of the cannula taken along line 7B—7B in FIG. 7A, FIG. 7C is a plan view of the cannula, and FIG. 7D illustrates an alternate embodiment of the cannula;

FIG. 8 illustrates a second step in the surgery;

Corresponding reference characters indicate corresponding parts throughout the drawings.

DESCRIPTION OF A PREFERRED EMBODIMENT

Figure 1:
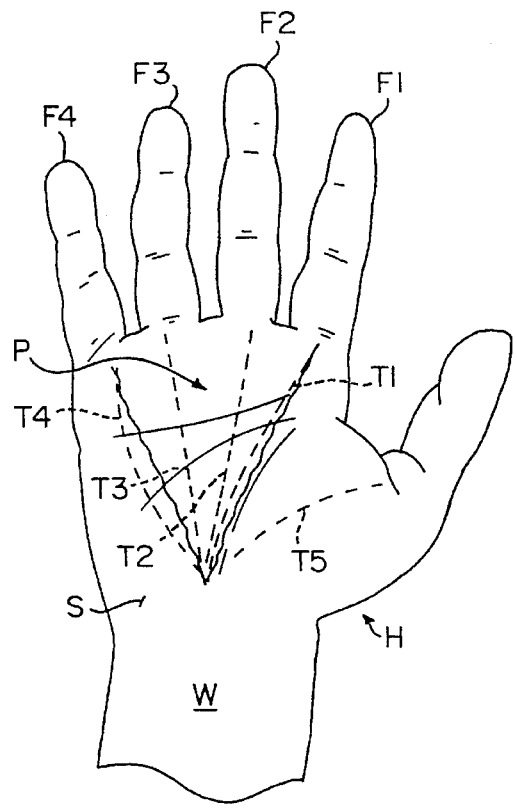
FIG. 1 is a view of the palm side of a hand with flexor tendons for various of the fingers being indicated.
Figure 3:
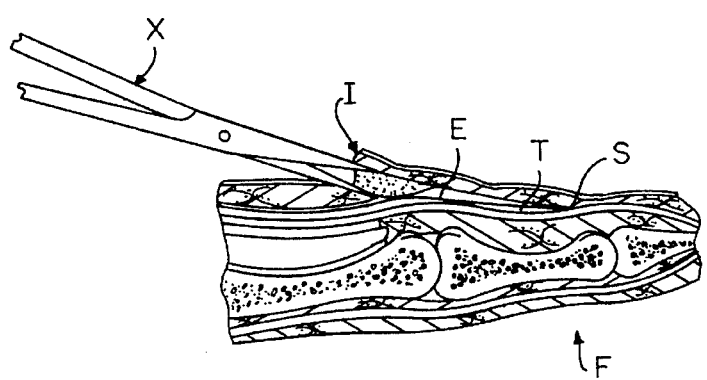
FIG. 3 is a partial cross-sectional view of the hand illustrating the surgical procedure.

Referring to the drawings, FIG. 1 illustrates a hand H having fingers F1–F4 and a thumb B. As indicated by the dashed lines in FIG. 1, tendons commonly referred to as flexor tendons T1–T5 extend beneath the skin S on the palm P of the hand to each of the fingers and thumb. As seen in FIG. 3, each flexor tendon is surrounded by a protective sheath E. Movement of the tendons produces flexure of the fingers as the hand is manipulated. A condition known as trigger finger occurs when the sheath is constricted about the tendon. This constriction results from formation of nodules (not shown) among other causes.

Figure 2:
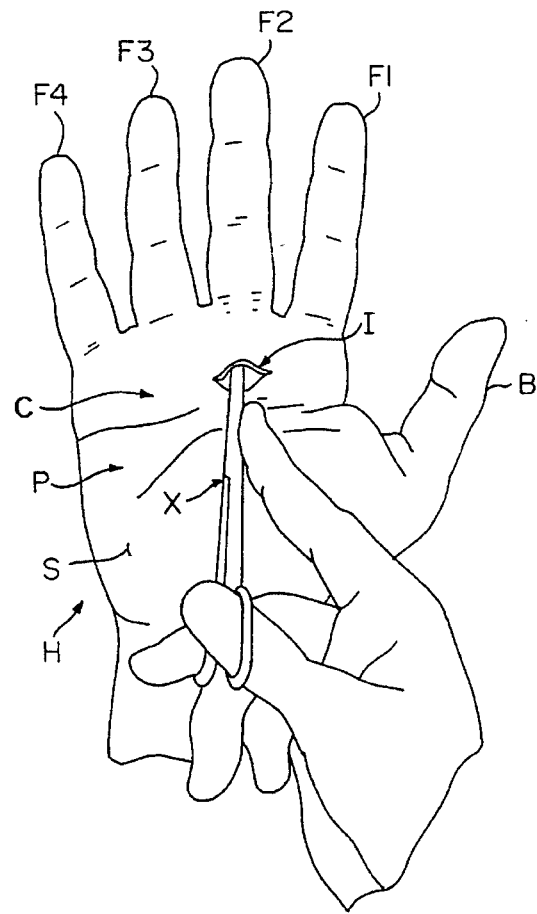
FIG. 2 shows the hand with a conventional trigger finger release procedure being performed on one of the flexor tendons.
Figure 4:
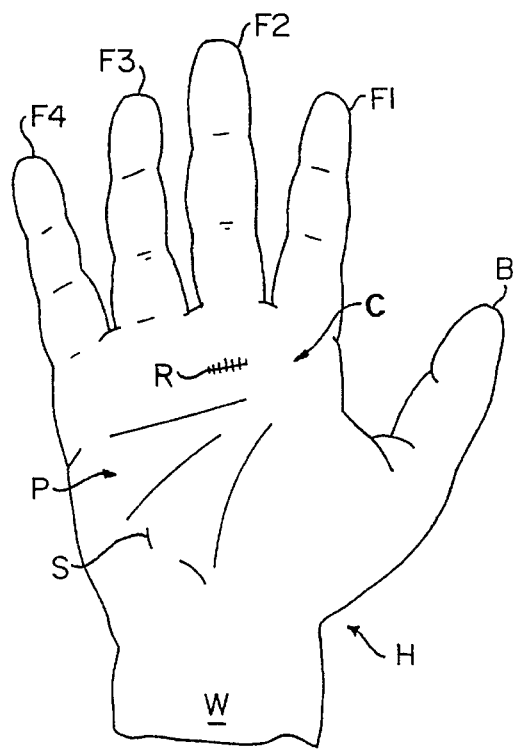
FIG. 4 is a view of the hand after the surgery has been performed.

FIGS. 2 and 3 illustrate a conventional surgical technique and surgical instruments for use in repairing trigger finger. As shown in FIG. 2, an incision I is made in the palm of the hand adjacent the distal crease C in the palm. A scissors X, scalpel, or other cutting instrument is inserted through the incision. The cutting instrument is used to cut open the sheath or annulus covering the tendon. This relieves the constriction. After withdrawal of the cutting instrument, the incision is sewn shut. After healing, the person on whom the operation is performed is left with a scar R such as shown in FIG. 4. While presence of a scar does not necessarily effect the person's ability to use their hand, it is unsightly, and can be avoided.

Referring now to FIGS. 5–9, a surgical method as described in my U.S. Pat. No. 5,353,812, is for performing trigger finger release surgery using an arthroscopic surgical technique. The advantage of this surgical procedure over that shown in FIGS. 2 and 3 is that while it is easy to perform, it allows the surgeon a better view of the surgical site, enables the surgeon to make a more precise cut of the pulley or sheath surrounding the tendon; and, after the surgery is completed, leaves no residual, unsightly scars.

Figure 5:
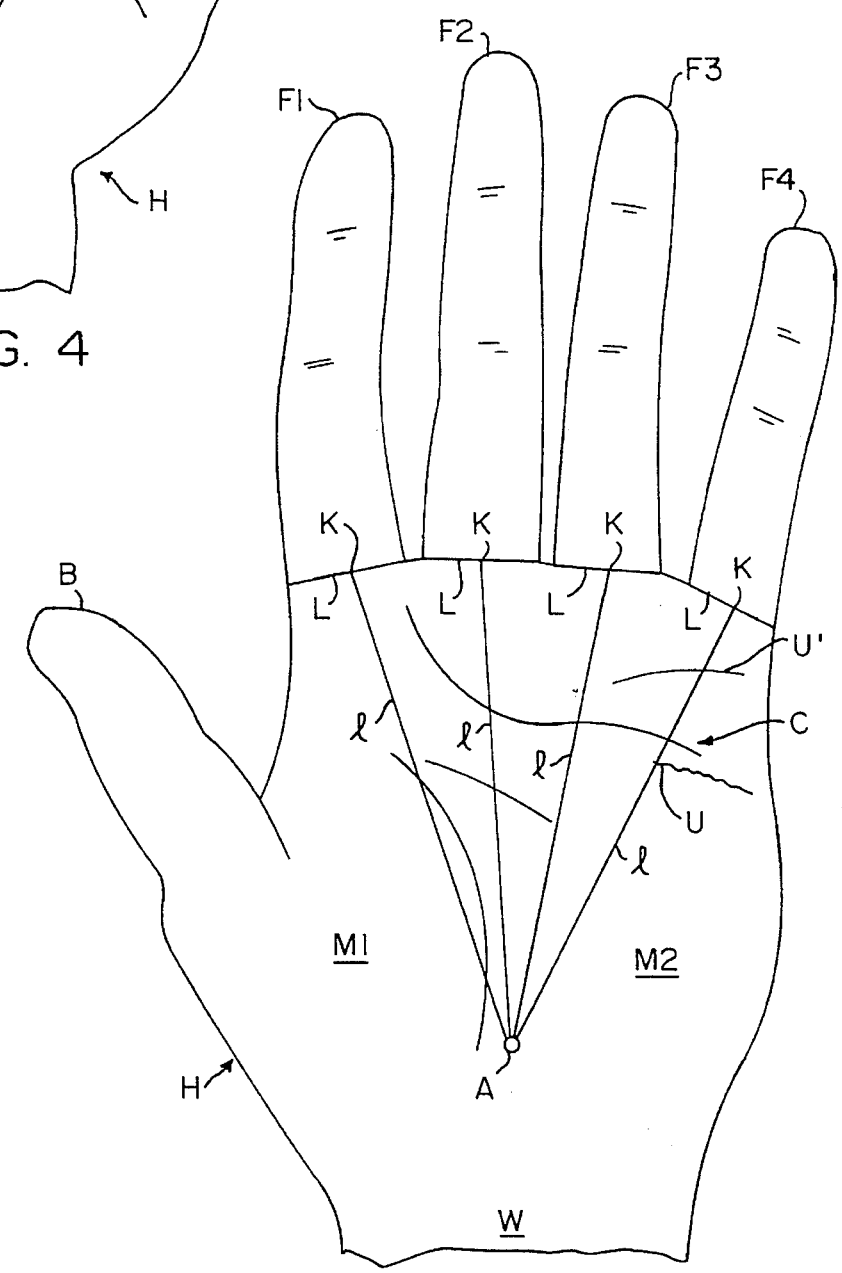
FIG. 5 is a view of a hand illustrating how flexor tendons going to each finger are located in accordance with the surgical method of the present invention.

The first step in performing the surgery is to identify the path of the flexor tendon to the effected finger. In FIG. 5, this is shown to be done by first locating a point A at the base of the palm where the hand joins with the wrist W. This reference point is found to be at the center of the thenar and lesser thenar muscles M1 and M2 respectively. Next, a line L is drawn across the base of the finger and the midpoint of this line marked as indicated at K. Finally, a line 1 is drawn from point A to point K. The flexor tendon T for the respective finger generally follows a path through the palm corresponding to the line 1 drawn on the skin of the palm.

The next step in the procedure is to locate along line 1 a puncture site U for inserting a surgical instrument 1 of the invention into the palm. Typically, the constriction in the sheath is found to be caused by a nodule. And, this nodule usually occurs where the flexor tendon crosses the distal crease C in the palm of the hand. Therefor, puncture site U will usually be adjacent the distal crease. AS seen in FIG. 5, site U is toward the reference point A side of the distal crease.

Referring to FIGS. 6, and 7A–7C, a surgical instrument 1 of the present invention is shown to be a hollow, curved cannula. The cannula is generally circular in cross-section and is, for example, only 1.5 mm.–2.5 mm in diameter. Further, the cannula has an arcuate or concave profile with the distance from one end of the cannula to the other being, for example, 25 mm. Further, the cannula has longitudinally extending slot 2 formed along the inner curved surface 3 of the cannula. Thus, as seen in FIG. 7B, the cannula has a general C-shape when viewed in cross-section. Slot 2 extends the entire length of the cannula. The outer curved surface 4 of the cannula is solid along the length of the instrument. As shown in FIG. 6, a trocar 5 is inserted in one end (the forward end) of the cannula. After fitting the trocar in the cannula, the surgeon siezes the cannula in a holder 6 and inserts the trocar end of the cannula into the palm of the hand at the selected site U. The surgeon then pushes the trocar end of the cannula through the palm of the hand until it comes back out through the skin making a second puncture hole U' in the skin at the exit site. The path 8 described by the cannula as it is pushed through the palm of the patient's hand passes through the sheath surrounding the flexor tendon.

Figure 12:
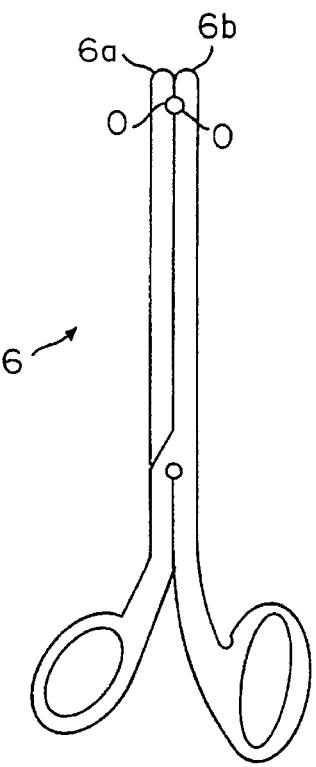
FIG. 12 is a plan view of a holder used by the surgeon to grasp the cannula and insert through the patient's palm; and, FIGS. 13A and 13B ilustrate use of a surgical knife to cut a sheath about the tendon and release the trigger finger.

It will be understood that the forward end 1a of cannula 1 can be blunt and sized for ready insertion of one end of trocar 5 into this end of the cannula. Alternatively, and as shown in FIG. 7D, the forward end of a cannula 1' can be pointed or bullet tipped as indicated at 1a'. With this latter forward end configuration, a trocar is still used to insert the cannula through the palm. Rather, the forward end of the cannula is sharp enough to be easily inserted through the palm. In either embodiment, the other end 1b or 1b' of the cannula is blunt. Further, as shown in FIG. 12, cannula 1 or 1' is inserted through the palm using the holder 6. The holder has a clamp end with opposed jaws 6a, 6b in each of which is formed a semicircular opening O. The diameter of these openings generally conforms to the diameter of the cannula. This allows the surgeon to use the opposed handle end of the holder to grasp the cannula, insert the cannula through the palm, and then release the cannula. At the conclusion of the surgery, the surgeon again uses the holder to grasp the cannula and remove it from the patient's palm.

After completing insertion of the cannula through the palm, both ends 1a, 1 b of the cannula are now extending out from the patient's hand. This is the condition shown in FIG. 8. If the surgeon used a cannula 1, he or she now removes the trocar from the one end of the cannula, being careful to leave the cannula in place. The surgeon then inserts an arthroscope 9 into one end of the cannula, and pushes the arthroscope forward through the cannula until it is adjacent the site of the constriction. Arthroscope 9 is comprised of a flexible bundle of fiber optic cables OC which are routed to a monitor 10. Use of the arthroscope allows the surgeon performing the method of the invention to view the surgical site. For this purpose, the surgeon feeds the fiber optic bundle through end 1b of the cannula until the forward end of the bundle is adjacent the area of the sheath or pulley which is to be cut. The surgeon views the site through the slot 2 in the cannula.

Figure 11:
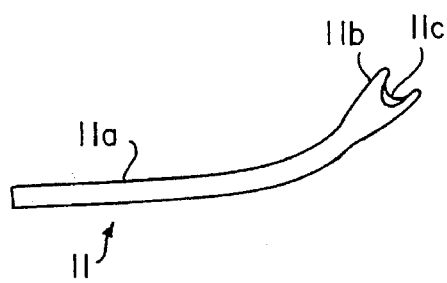
FIG. 11 illustrates a surgical knife of the invention which is inserted into the other end of the cannula and with which the surgeon can release the trigger finger.
Figure 13A:
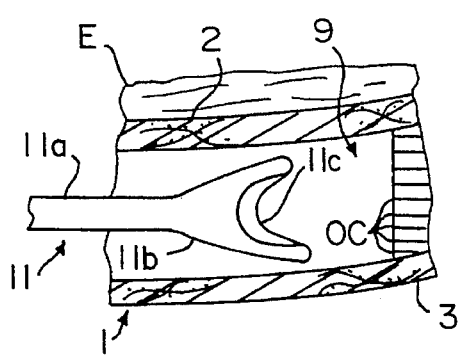

Next, the surgeon inserts a curved or flexible surgical knife 11 into the opposite end (end 1a) of the cannula. The surgeon pushes the knife forward into the cannula until it is immediately beneath the portion of the sheath or pulley to be cut in order to relieve the constriction on the tendon and release the trigger finger. As shown in FIG. 11, knife 11 has a shank portion 11a which can be grasped by the surgeon to manipulate the knife. For this purpose, the surgeon may use a holder similar to holder 6. That is, the holder has jaws with respective openings by which the shank of the knife can be grasped by the surgeon. The surgeon then moves the knife by manipulating the shank with the holder. Knife 11 also has an enlarged head 11b the thickness of which is narrower than the width of slot 2 in cannula 1. The height of the head is greater than the diameter of shank 11a; but, again, is less than the diameter of the cannula for the head to be insertable in the cannula. This is the condition shown in FIG. 13A.

Figure 13B:
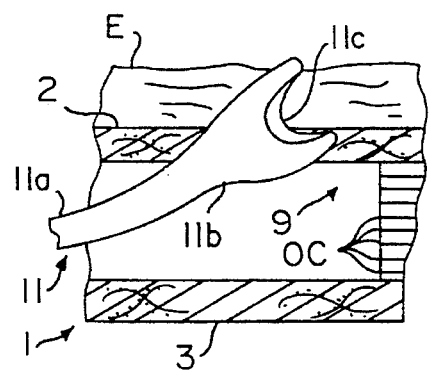

The head of the knife is widest at its outer end. The outer end of the knife has an inward or concave cutting edge 11c. The length of the cutting edge is shorter than the height of the knife at its outer end. This means the surgeon must rotate the knife through slot 2 in the cannula to bring the cutting edge to bear against the sheath. This is as shown in FIG. 13B.

Using the arthroscope to guide him or her, the surgeon proceeds to make the appropriate cuts in the pulley or sheath. This is done by the surgeon moving the cutting edge of the knife from its FIG. 13A to its FIG. 13B position and moving the knife through the slot in the cannula. As the cut or cuts are made in the annulus of covering material about the tendon, the restriction is relieved and the trigger finger released.

Figure 9:
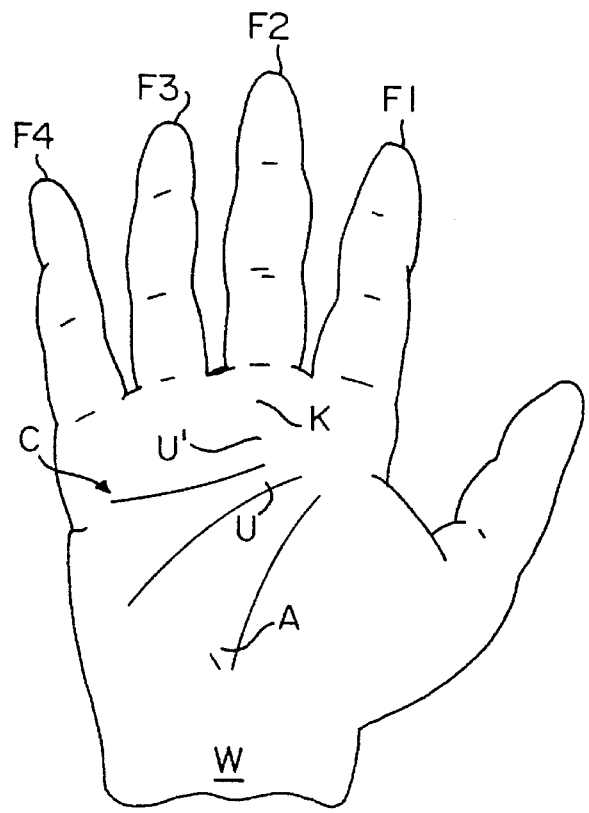
FIG. 9 is a view of the hand similar to FIG. 4 and illustrating its condition after the surgical procedure of the present invention is completed.
Figure 10:
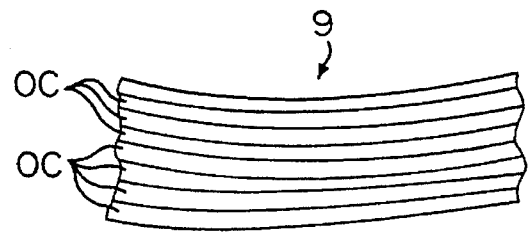
FIG. 10 represents an arthroscope inserted into one end of the cannula to enable a surgeon to view the surgical site.

When finished, the surgeon withdraws knife 11 from the one end of the cannula. He or she then withdraws arthroscope 9 from the other end. Next, the cannula is withdrawn from the patient's palm. One of the benefits of the surgical technique described is that because of the size of the cannula, puncturewounds U and U' do not require stitches to close them. And, as the puncture wounds heal, no scars are formed. Thus, as shown in FIG. 9, the holes U and U' made in the patient's hand are quite small compared with the incision I made as part of the conventional surgical procedure, and the resulting scar R seen in FIG. 4.

What has been described is a surgical procedure for use in relieving the trigger finger or trigger thumb condition of a patient. The procedure is an endoscopic surgical procedure. In performing the procedure a reference point is first located at the center of the thenar and lesser thenar muscles in the palm of the hand. After the routing of the flexor tendon going to each finger and thumb is determined using the reference point, an appropriate incision site is located. The skin is then punctured at first and second spaced spaced sites. An endoscopic surgical instrument which is a curved, slotted cannula which may have an attached trocar is used to accomplish this. The cannula is left in place for use with a surgical knife by which the distal palm pulley causing the trigger finger is severed. An arthroscope is fitted in one end of the cannula to provide the surgeon a view of the surgical site. A surgical knife devised for use in this type surgery is inserted in the opposite end of the cannula and is used to make cuts in the sheath surrounding the constricted tendon to release the constriction. The punctures made in the palm of the hand by insertion of the cannula are sufficiently small that after completion of the surgery and removal of the cannula, no sutures are required to close the puncture holes. As healing takes place, no scars are formed in the palm of the hand. The endoscopic procedure can be performed by a surgeon as readily as previous surgical procedures used to effect similar repairs. Finally, the surgery can be performed at any convenient location such as the surgeon's office, a clinic, or a hospital and its performance only involves an attending physician and a surgical nurse or aide.

In view of the foregoing, it will be seen that the several objects of the invention are achieved and other advantageous results are obtained.

As various changes could be made in the above constructions without departing from the scope of the invention, it is intended that all Matter contained in the above description or shown in the accompanying drawings shall be interpreted as illustrative and not in a limiting sense.

Having thus described the invention, what is claimed and desired to be secured by Letters Patent is:

1. A surgical kit for performing trigger finger release surgery by which a sheath covering a constricted flexor tendon in a patient's hand is cut to relieve the constriction and release the trigger finger comprising:

a cannula having one end insertable through the skin covering the palm of the patient's hand, said cannula being a hollow, concavely curved instrument which by continued insertion of said insertable end into the palm causes said insertable end to be pushed back out through the skin covering the palm whereby a first puncture wound is made in the skin at an entry site of the cannula and a second puncture wound is made at an exit site thereof, said cannula being adapted to be pushed through the palm of the hand such that the path of said cannula passes through said sheath, said cannula further adapted to being left in place after its insertion, and said cannula being curved along its longitudinal axis and having a longitudinal slot formed on its inner curved surface, said slot extending from said insertable end of the cannula to the other end thereof;

an arthroscope insertable in one end of said cannula for allowing an operating surgeon to view the surgical site; and, a curved, flexible surgical knife insertable in the cannula end opposite to that which an arthroscope is inserted said surgical knife being used by the surgeon to cut said sheath and release the trigger finger with said surgical site being viewable using said arthroscope, said arthroscope and said knife being withdrawn from said cannula after said sheath is cut, and said cannula being withdrawn thereafter, and the diameter of said cannula being such that after its withdrawal, said first and second puncture wounds do not require stitches to close them, and, as said wounds heal, no scars are formed.

2. The kit of claim 1 wherein said cannula is generally circular in cross-section.

3. The kit of claim 2 further including a trocar inserted in said insertable end of the cannula for inserting the cannula through the palm of the patient's hand.

4. The kit of claim 2 wherein said insertable end of said cannula is pointed for inserting said cannula through said patient's palm.

5. The kit of claim 2 further including a holder for grasping said cannula and inserting it through said patient's palm, said holder having one end at which opposed jaws are formed and a second end at which handles are formed, said handles being graspable by said surgeon for opening and closing said jaws, and said jaws having opposed semicircular openings formed therein the diameter of each of which approximates the diameter of the cannula for the cannula to be held in the jaws during insertion into the palm by said surgeon.

6. The kit of claim 1 wherein said arthroscope includes a flexible fiber optical bundle and a monitor to which said bundle is connected for said surgeon to view said surgical site on said monitor.

7. The kit of claim 1 wherein said surgical knife includes a curved, flexible shank graspable by a holder for said surgeon to insert said knife in said slot in said cannula using said holder; and an enlarged head at the end of said shank inserted in said cannula, said knife head having a cutting edge formed thereon.

8. The kit of claim 7 wherein said cutting edge is formed at an outer end of said knife head, said cutting edge having a length which is less than a height of the knife at said outer end of said head.

9. An arthroscopic surgical kit comprising:

a cannula having one end insertable into a patient's skin at an entry site, the cannula having a hollow, concave body by which continued insertion of the cannula body through the skin causes the inserted end of the cannula to be pushed back through the patient's skin at an exit site, the cannula adapted to remain in the patient, and the cannula having a slot formed along an inside, curved surface of the cannula body and extending the entire length of the body from one end of the cannula to the other, and the cannula being inserted in the patient's body at a location where an arthroscopic surgical procedure is to be performed;

an arthroscope insertable into one end of the cannula for viewing the patient's tissue along the path defined by the cannula body; and, a surgical knife having a flexible shank for inserting a cutting end of the knife into the other end of the cannula body, the knife having a cutting edge formed at said cutting end which is manipulable by a surgeon to cut tissue adjacent the slot in the cannula body.

* * * * *